United States Patent [19]

Welstead, Jr.

[11] 4,002,766
[45] Jan. 11, 1977

[54] ANTIARRHYTHMIA METHODS

[75] Inventor: William John Welstead, Jr., Richmond, Va.

[73] Assignee: A. H. Robins Company, Inc., Richmond, Va.

[22] Filed: Dec. 26, 1974

[21] Appl. No.: 536,708

[52] U.S. Cl. .......................... 424/274; 424/248.57
[51] Int. Cl.² ...................................... A61K 31/40
[58] Field of Search .............. 424/274; 260/326.5 C

[56] References Cited
UNITED STATES PATENTS

| | | | |
|---|---|---|---|
| 3,192,210 | 6/1965 | Lunsford et al. | 260/247.2 |
| 3,466,321 | 9/1969 | Morren | 260/471 |
| 3,878,217 | 4/1975 | Carr | 260/293.64 |

Primary Examiner—Leonard Schenkman

[57] ABSTRACT

1-R-3-Pyrrolidinyl-α,α-diphenylacetamides, -acetonitriles and -methanes represented by the following formula:

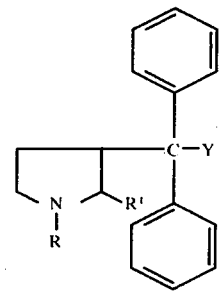

wherein R represents hydrogen, lower alkyl, lower cycloalkyl or phenyllower alkyl, R¹ represents hydrogen or lower alkyl, and Y is carbomoyl, di-lower-alkyl-carbamoyl, pyrrolidinocarbonyl, morpholinocarbonyl, cyano or hydrogen having antiarrhythmic activity are disclosed. Pharmaceutically acceptable acid addition salts are included as part of the invention.

5 Claims, No Drawings

ANTIARRHYTHMIA METHODS

FIELD OF INVENTION

The present invention relates to certain heterocyclic organic compounds which may be referred to as $\alpha,\alpha,\alpha$-trisubstituted acetamides-, acetonitriles and -methanes and is more particularly concerned with 1-R-3-pyrrolidinyl-$\alpha,\alpha$-diphenylacetamides, -acetonitriles and -methanes, compositions containing the same as active ingredients and methods of using them.

Certain compounds in the present application, especially the 1-R-3-pyrrolidinyl-$\alpha,\alpha$-diphenylacetamides (and -acetonitriles) are disclosed as intermediates in U.S. Pat. Nos.: 3,192,206; 3,192,210; 3,192,221 and 3,102,230.

SUMMARY OF INVENTION

The present invention is especially concerned with heterocyclic organic compounds, compositions containing said compounds as active ingredients and methods of using said compositions in controlling cardiac arrhythmias, said compounds having the formula:

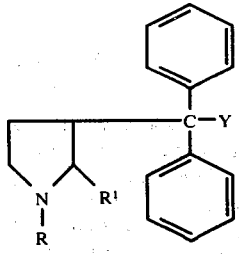

Formula I wherein;
R is hydrogen, lower alkyl, lower cycloalkyl, or phenyl-lower alkyl;
$R^1$ is hydrogen or lower alkyl,
Y is carbamoyl, di-lower-alkylcarbamoyl, pyrrolidinocarbonyl, morpholinocarbonyl, cyano or hydrogen, and the pharmaceutically acceptable acid addition salts thereof.

A preferred group of compounds are those of Formula I wherein R is hydrogen, lower alkyl, lower cycloalkyl or phenyl lower alkyl, R' is hydrogen or lower alkyl and Y is carbomoyl, cyano or hydrogen.

DETAILED DESCRIPTION OF INVENTION

The compounds described hereinafter and represented by the foregoing Formula I have been shown by accepted pharmacological procedures to have utility as physiologically active agents, and particularly as effective antiarrhythmic agents, therapeutically applicable in the treatment of cardiac arrhythmias.

The action of certain compounds disclosed in the present invention in counteracting cardiac arrhythmia is demonstrated by the following procedure. The procedure is carried out under barbiturate anesthesia using adult mongrel dogs of either sex weighing from 8 to 14 kg. A Grass Model 7 polygraph was used for recording femoral arterial blood pressure (Statham P23AC transducer) and the electrocardiagram (Grass 7P4 preamplifier). Ouabain was given intravenously in an initial dose of 40$\gamma$/kg, in a second dose of 20$\gamma$/kg, given 30 minutes after the first dose, and in subsequent doses of 10$\gamma$/kg which were repeated at 15 minute intervals as required for producing cardiac arrhythmias that persisted for at least 15 minutes. When the arrhythmias were established the test compounds were administered by infusion (Harvard Model 942 infusion pump) into a femoral vein at a rate of 1 mg/kg/min. Concentrations of compounds were adjusted according to the weight of the dog to allow a volume infusion of 1 ml/min. Compounds that are considered to be active as antiarrhythmic agents cause reversion to sinus rhythm which is maintained for at least 60 minutes.

Examples 3, 7 and 8 represent preferred compounds and the $ED_{50}$'s (mg/kg, i.p.) of the respective compounds are 2.0, 4.25 and 3.25.

It is, accordingly, an object of the present invention to provide compounds with a high degree of antiarrhythmic activity. An additional object is the provision of compounds having antiarrhythmic activity and which produce minimal side effects. A further object is to provide pharmaceutical compositions containing the compounds as active ingredients. A still further object is to provide a method of using said antiarrhythmic agents in the treatment of living animal and especially mammalian bodies. Additional objects will be apparent to one skilled in the art, and still other objects will become apparent hereinafter.

The invention also includes pharmaceutically acceptable acid addition salts of the above bases and the optical isomers thereof which are formed with nontoxic organic and inorganic acids. Such salts are usually prepared by methods known to the art. The base is reacted with either the calculated amount of organic or inorganic acid in aqueous miscible solvent, such as ethanol or isopropanol, with isolation of the salt by concentration and cooling or with an excess of the acid in an aqueous immiscible solvent, such as ethyl ether or isopropyl ether, with the desired salt separating directly. Exemplary of such organic salts are those with maleic, fumaric, benzoic, ascorbic, tartaric, malic, and citric acid and the like. Exemplary of such inorganic salts are those with hydrochloric, hydrobromic, sulfuric, phosphoric and nitric acids.

In the definitions of symbols in the foregoing Formula I and where they appear elsewhere throughout this specification, the terms have the following significance.

The term "loweralkyl" as used herein includes straight and branched chain radicals of from 1 to 8 carbon atoms inclusive. Examples of loweralkyl radicals are methyl, ethyl, propyl, n-butyl, isopropyl, isobutyl, amyl, isoamyl, hexyl, heptyl, octyl, isooctyl, and the like.

The term "lower cycloalkyl" as used herein includes primarily cyclic radicals containing 3 to 9 carbon atoms inclusive and encompasses such groups as cyclopropyl, cyclobutyl, cyclopentyl, cyclohexyl, methylcyclohexyl, propylcyclohexyl, cycloheptyl, and cyclooctyl.

The term "phenyl-loweralkyl" as used herein includes lower-alkyl, substituted phenyl groups such as benzyl, penethyl, methylbenzyl, phenpropyl, and the like.

The starting material for some of the compound of the present invention is $\alpha,\alpha$-diphenylacetonitrile (II). Some of the compounds of Formula I are thusly prepared by reacting $\alpha,\alpha$-diphenylacetonitrile with a selected 1-R-3-halopyrrolidine (III) or a 1-R-3-pyrrolidinyl tosylate (III) to give 1-R-3-pyrrolidinyl-$\alpha,\alpha$-diphenylacetonitrile. The thusly prepared acetonitriles are within the scope of Formula I and also serve as intermediates for the preparation of the 1-R-3-pyrrolidinyl-α,α-diphenylacetamides and the 1-R-3-pyrrolidinyl-α,α-diphenylmethanes of Formula I. The foregoing reactions are in accord with the following graphic reaction sequence:

rolidine V with a selected 3-halopyrrolidine III or 3-pyrrolidinyltosylate III is applicable for other diphenylacetylheterocycles as, for example, diphenylacetylmorpholine and diphenylacetylpiperidine.

The 1-R-3-pyrrolidinyl-α,α-diphenylacetonitriles I

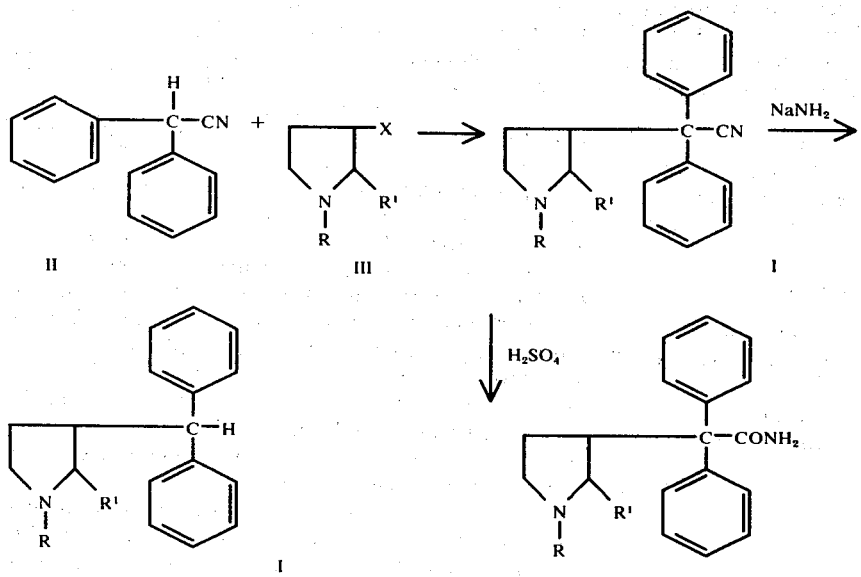

wherein R and R¹ have the values assigned hereinabove, Y of general Formula I is shown as —CN, —CONH₂, and —H and X is a halide, preferably chlorine or a tosylate group.

Some of the compounds of Formula I and in particular those compounds wherein Y is an amido radical may be prepared by a process illustrated by the following equations:

are generally prepared by alkylating the alkali metal, e.g., sodium salt of α,α-diphenylacetonitrile with the appropriate 1-R-3-halo (e.g., chloro) pyrrolidine or the appropriate 1-R-3-pyrrolidinyltosylate in a suitable solvent such as dry toluene. The sodium salt of α,α-diphenylacetonitrile is formed by reaction of the nitrile with an alkali metal amide, e.g., sodamide in a dry solvent, e.g., toluene. The condensation with the 3-

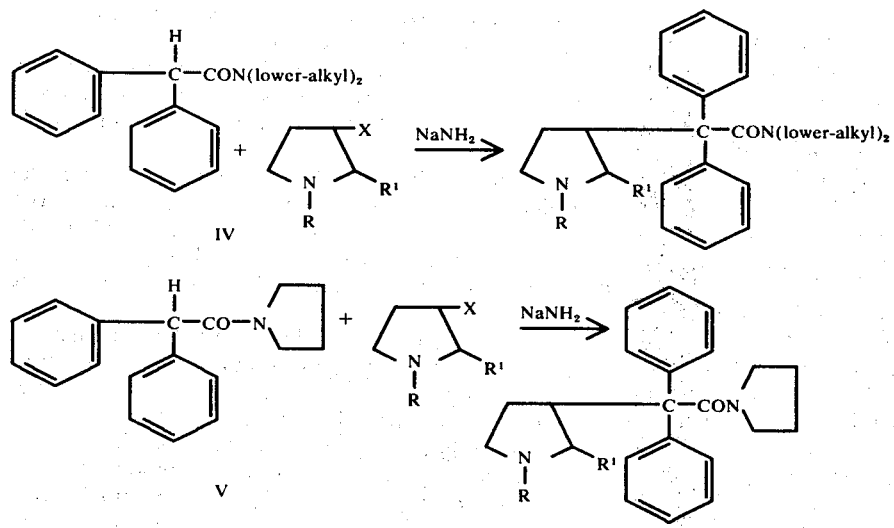

The processes illustrated above are carried out as described more fully hereinafter for the preparation of a 1-R-3-pyrrolidinyl-α,α-diphenylacetamide wherein an N,N-diloweralkyl-α,α-diphenyl acetamide IV or a diphenylacetylpyrrolidine V is first metalated in a dry aprotic solvent using sodamide and the salt is then reacted with a selected 3-halopyrrolidine or a 3-pyrrolidinyltosylate. The reaction of diphenylacetylpyrrolidine V with a selected 3-halopyrrolidine III or 3-pyrrolidinyltosylate III is applicable for other diphenylacetylheterocycles as, for example, diphenylacetylmorpholine and diphenylacetylpiperidine.

chloropyrrolidine or the 3-pyrrolidinyltosylate is usually carried out with the application of heat, e.g., in refluxing benzene, toluene, or like solvent for an extended period, e.g., approximately 3 hours. The solvent, e.g., toluene solution, is then washed with water and the product extracted as with one normal hydrochloric acid. The acid extract may then be basified with sodium hydroxide, extracted with a water-insoluble solvent such as ether or chloroform, the solution washed and dried, as over sodium sulfate, concentrated, and then the residue distilled in vacuo.

The 1-R-3-pyrrolidinyl-α,α-diphenylacetonitriles are heated in concentrated sulfuric acid for a period of from about 15 hours to about 30 hours at a temperature of from about 50° C. to about 80° C., preferably at 60° C. to 70° C. The acidic mixture is cooled and maintained below about 50° C. while the solution is basified using a strongly basic solution as, for example, 50% sodium hydroxide; the acetamide products are extracted with a suitable solvent such as chloroform or ethyl acetate, the extract concentrated and the products allowed to separate from the concentrated solutions.

The 1-R-3-pyrrolidinyl-α,α-diphenylmethanes of Formula I are prepared by refluxing a mixture of the precursor acetonitriles and sodium amide in a dry aprotic solvent as, for example, toluene, for a period of from about 20 hours to about 30 hours. The cooled mixtures are diluted with water, the organic layers separated, dried over a suitable drying agent such as sodium sulfate, the dried solutions filtered and concentrated and the residual products isolated by a suitable procedure such as vacuum distillation or conversion to an acid addition salt which is further purified by crystallization.

Compounds of Formula I wherein R is hydrogen are prepared by shaking a compound wherein R is benzyl in three atmospheres of hydrogen using a palladium-on-charcoal catalyst. The compounds wherein R is benzyl are prepared by using 1-benzyl-3-halopyrrolidines as reactants.

EXAMPLE 1

α,α-Diphenyl-α-(1-isopropyl-3-pyrrolidinyl)acetonitrile

In a 2 liter, three neck, round-bottom flask fitted with pot thermometer, reflux condensor, electric stirrer and dropping funnel was placed 47.5 g (1.22 mole) of sodium amide followed by 300 ml. of dry toluene. To this was added dropwise at 50° C. 214 g. (1.11 mole) of diphenylacetonitrile in 800 ml. of dry toluene. When addition was complete, the temperature was raised slowly to reflux and maintained for 4 hours. To the refluxing mixture was added at a rapid dropwise rate 164.9 g. (1.11 mole) of 1-isopropyl-3-chloropyrrolidine. The refluxing and stirring was continued for 3 hours, and the mixture was allowed to stand overnight. The toluene solution was washed with 1 liter of water and extracted with about 2 liters of 1 N hydrochloric acid. The aqueous layer was made basic with dilute sodium hydroxide and extracted with several portions of ether. The ethereal solution was dried over sodium sulfate, concentrated, and the residue distilled through an eight inch beaded column. Yield, 216 g. (64%); b.p. 175°–177° C./0.25 mm. The product crystallized on standing and was recrystallized from iso-octane. M.p. 73°–74° C.

Analysis: Calculated for $C_{21}H_{24}N_2$: C,82.85; H,7.95; N,9.20; Found: C,82.88; H,7.89; N,9.05.

EXAMPLE 2

α,α-Diphenyl-α-(1-ethyl-3-pyrrolidinyl)acetamide

To 240 ml. of concentrated sulfuric acid was added 60 g. (0.21 mole) of α,α-diphenyl-α-(1-ethyl-3-pyrrolidinylacetonitrile. The mixture was shaken until solution took place and allowed to stand at 70° C. for 24 hours. The solution was poured on ice, made basic with ammonium hydroxide and extracted with about 1000 ml. of ethyl acetate. The ethyl acetate solution was dried with anhydrous sodium sulfate and concentrated to about 200 ml. The white crystals that were obtained on cooling were recrystallized from an ethyl acetate-ligroin mixture. Yield 34 g. (52.5%); m.p. 141°–142° C.

Analysis: Calculated for $C_{20}H_{24}N_2O$: C,77.88; H,7.84; N,9.09; Found: C,79.70; H,8.18; N,8.83.

EXAMPLE 3

α-(1-Cyclohexyl-3-pyrrolidinyl)-α,α-diphenylacetamide

To 80 ml. of concentrated sulfuric acid was added 20 g. (0.057 mole) of α-(cyclohexyl-3-pyrrolidinyl)-α,α-diphenylacetonitrile. The mixture was shaken until solution occurred while being cooled in an ice bath until heat was no longer evolved. The solution was heated at 70° C. for 48 hours, poured on ice and made basic with ammonium hydroxide. The resulting white solid precipitate was taken up in ethyl acetate and the solution dried over sodium sulfate. The solution was concentrated and the residual oil taken up in hot ligroin, filtered and allowed to stand overnight at room temperature. The resulting crystals were recrystallized from ligroin. Yield 9.0 g. (42.5%); m.p. 119°–121° C.

Analysis: Calculated for $C_{24}H_{30}N_2O$: C,79.51; H,8.34; N,7.73; Found: C,79.69; H,8.51; N,7.58.

EXAMPLE 4

N,N-Dimethyl-α,α-diphenyl-α-(1-methyl-3-pyrrolidinyl) acetamide

To a suspension of 20 g. (0.5 mole) of sodamide in 750 ml. of dry toluene was added dropwise 50.58 g. (0.5 mole) of 1-methyl-3-pyrrolidinol with cooling below 30° C. After stirring for 1 hour, 95.32 g. (0.5 mole) of p-toluene sulfonyl chloride in 500 ml. of dry toluene was added rapidly at a temperature below 10° C. maintained by dry ice/acetone bath. The temperature was allowed to come to room temperature and stirred for 2 hours. The reaction mixture was cooled, washed with 500 ml. of cold water and the toluene layer was dried over calcium sulfate, filtered and the dried toluene solution concentrated at reduced pressure. To 93.5 g. (0.39 mole) of N,N-dimethyl-α,α-diphenylacetamide in 500 ml. of dry toluene was added 15.6 g. (0.4 mole) of sodamide and the mixture was slowly brought to reflux with stirring. After refluxing for 3 hours, the tosylate in 250 ml. of dry toluene was added at a convenient rate to the refluxing reaction mixture which was then refluxed for 3 hours. The resulting suspension was filtered and the toluene filtrate was evaporated under water pump vacuum, leaving an oil which on cooling became semi-crystalline and was taken into 6N hydrochloric acid. The acid solution was extracted with ether, made basic with 6N sodium hydroxide and the base insoluble oil extracted with ether. The ether extracts were dried over calcium sulfate, filtered, and evaporated leaving an amber oil. The product was distilled at 175°–180° C./0.005 mm. to give 22 g. (38%) of product.

EXAMPLE 5

N,N-Dimethyl-α,α-diphenyl-α-(3-pyrrolidinyl)acetamide

A solution containing 25.2 g. (0.0720 mole) of N,N-dimethyl-α,α-diphenyl-α-(1-isopropyl-3-pyrrolidinyl) acetamide, 14.3 g. (0.153 mole) of phosgene, and 7.27 g. (0.0720 mole) of triethylamine in 275 ml. of benzene was stirred at room temperature for one hour. After extraction with dilute acid the benzene layer produced 25.6 g. of neutral material which showed a good carbamoyl chloride band at 5.85 μ. The material was hydrolyzed in refluxing 10% sulfuric acid for one hour to give 19.5 g. of crude product. Acid-base extraction removed some neutral material and the free base was converted to the fumarate salt which was recrystallized from ethanol-isopropyl ether; m.p. 159°–160° C.

Analysis: Calculated for $C_{24}H_{28}N_2O_5$: C,67.90; H,6.65; N,6.60; Found: C,67.81; H,6.61; N,6.47.

EXAMPLE 6

1-[α,α-Diphenyl-α-(1-methyl-3-pyrrolidinyl)acetyl]-pyrrolidine

A mixture containing 10 g. (0.0377 mole) of 1-diphenylacetylpyrrolidine in 60 ml. of dry toluene and 1.60 g. (0.0411 mole) of sodamide was stirred at reflux for about 45 min. until ammonia evolution (0.0355 mole) had ceased. To the solution was added 0.0377 mole of 1-methyl-3-pyrrolidinolbenzenesulfonate in 30 ml. of dry toluene and the resulting slurry was stirred at reflux overnight. Acid-base extraction gave 4.10 g. of starting amide and 9.00 g. of crude amine fraction. Chromatography on magnesium sulfate (300 g.) gave 4.42 g. of pure product which melted at 137°–140° C. after crystallization from isopropyl ether.

Analysis: Calculated for $C_{23}H_{28}N_2O$: C,79.27; H,8.10; N,8.04; Found: C,79.07; H,8.02; N,8.10.

EXAMPLE 7

3-Benzhydryl-1-isobutylpyrrolidine Maleate

To a solution of 41.3 g. (0.13 mole) of α,α-diphenyl-α-(1-isobutyl-3-pyrrolidinyl)acetonitrile in 120 ml. of dry toluene was added 11.2 g. (0.286 mole) of sodium amide in a 500 ml. round bottom flask equipped with a reflux condenser and mechanical stirrer. The stirred mixture was refluxed for 46 hours. A large excess of water was added slowly and the water layer separated and discarded after being extracted with ether which was combined with the organic layer. The organic layer was washed with water and extracted with an excess of 2 N hydrochloric acid. The acid extract was basified with sodium hydroxide and the oil which separated was extracted with ether. The ethereal solutions were combined, concentrated and the residue was distilled. Yield, 25.8 g. (68%); b.p. 150°–152° C/0.05 mm. To 11.2 g. (0.0382 mole) of the above product was added 4.45 g. (0.0382 mole) of maleic acid in 150 ml. of absolute alcohol. After the amine dissolved, 100 ml. of dry ether was added. On standing in the refrigerator for several days the solution yielded a white solid which was recrystallized from ethyl acetate. Yield, 10.5 g. (67.25%); m.p. 119°–120° C.

Analysis: Calculated for $C_{25}H_{31}NO_4$: C,73.32; H,7.63; N,3.42; Found: C,73.58; H,7.59; N,3.55.

EXAMPLE 8

α,α-Diphenyl-α-(1-isopropyl-3-pyrrolidinyl)acetamide

A solution of 29.0 g. of α,α-diphenyl-α-(1-isopropyl-3-pyrrolidinyl)acetonitrile in 100 ml. of conc. sulfuric acid was heated at 80° C. for 18 hours. The reaction mixture was poured onto ice, the resulting cold acidic solution made basic using sodium hydroxide and the basic solution extracted with chloroform. The dried chloroform extract was concentrated and the residue crystallized from isooctane. The solid was recrystallized from isopropyl ether to give 13.2 g. (43%) of product which melted at 110.5°–112.5° C.

Analysis: Calculated for $C_{21}H_{26}N_2O$: C,78.22; H,8.13; N,8.57; Found: C,78.00; H,8.16; N,8.57.

The physical constants of additional compounds of Formula I prepared by the procedures set forth in detail in Examples 1–8 are as shown in Tables I and II.

Table I

Examples 9–25

| Example | R | R¹ | Y | M.P. (B.P. mm) °C |
|---|---|---|---|---|
| 9 | $CH_3$ | H | CN | 81–2 |
| 10 | $C_2H_5$ | H | CN | 83–4 |
| 11 | $i\text{-}C_4H_9$ | H | CN | 76–7 |
| 12 | $C_6H_{11}$ | H | CN | 90 |
| 13 | $C_6H_5CH_2$ | H | CN | 215–8/.01 |
| 14 | $CH_3$ | $CH_3$ | CN | 115–17 |
| 15 | $CH_3$ | H | $CONH_2$ | 154–4.5 |
| 16 | $n\text{-}C_3H_7$ | H | $CONH_2$ | 141.5–2.0 |
| 17 | $i\text{-}C_4H_9$ | H | $CONH_2$ | 85–8 |
| 18 | $i\text{-}C_3H_7$ | H | $CON(CH_3)_2$ | 185–90/.05 |
| 19 | $CH_3$ | H | $CON(C_2H_5)_2$ | — |
| 20 | $CH_3$ | H | $CONCH_2CH_2OCH_2CH_2$ | 114–18 |
| 21¹ | $CH_3$ | H | H | 78–80 |
| 22² | $C_2H_5$ | H | H | 60–3 |
| 23 | $i\text{-}C_3H_7$ | H | H | 94–5 |
| 24³ | $C_6H_{11}$ | H | H | 80–5 |
| 25 | $C_6H_5CH_2$ | H | H | 92–3 |

¹m.p. of maleate salt 123–4° C.;
²m.p. of maleate salt 102–3° C.;
³m.p. of maleate salt 159° C.

Table II

Analytical Data on Examples 9 to 25

| Example | Empirical Formula | Calculated | | | Found | | |
|---|---|---|---|---|---|---|---|
| | | C | H | N | C | H | N |
| 9 | $C_{19}H_{20}N_2$ | 82.57 | 7.29 | 10.14 | 82.82 | 7.45 | 9.72 |
| 10 | $C_{20}H_{22}N_2$ | 82.71 | 7.63 | 9.63 | 82.83 | 7.78 | 9.47 |
| 11 | $C_{22}H_{22}N_2$ | 85.19 | 6.86 | 7.95 | 84.93 | 6.93 | 7.75 |
| 12 | $C_{24}H_{29}N_2$ | 83.43 | 8.46 | 8.11 | 83.23 | 8.33 | 7.78 |
| 13 | $C_{25}H_{24}N_2$ | 85.19 | 6.86 | 7.95 | 84.93 | 6.93 | 7.75 |
| 14 | $C_{20}H_{22}N_2$ | 82.71 | 7.64 | 9.65 | 82.87 | 7.62 | 9.52 |
| 15 | $C_{19}H_{22}N_2O$ | 77.59 | 7.53 | 7.52 | 77.77 | 7.70 | 9.10 |
| 16 | $C_{21}H_{26}N_2O$ | 78.22 | 8.13 | 8.69 | 78.52 | 8.16 | 8.50 |
| 17 | $C_{22}H_{28}N_2O$ | 78.53 | 8.39 | 8.33 | 78.77 | 8.61 | 8.34 |
| 18 | $C_{23}H_{30}N_2O$ | 78.81 | 8.63 | 7.99 | 78.61 | 8.45 | 7.88 |
| 19 | $C_{23}H_{30}N_2O$ | 78.81 | 8.63 | 7.99 | 78.65 | 8.58 | 8.04 |
| 20 | $C_{23}H_{28}N_2O_2$ | 75.79 | 7.74 | 7.69 | 75.56 | 7.84 | 7.55 |
| 21¹ | $C_{18}H_{21}N$ | | | 5.57 | | | 5.70 |
| | $C_{22}H_{25}NO_4$ | 71.91 | 6.86 | | 72.13 | 6.84 | |
| 22² | $C_{19}H_{23}N$ | | | 5.28 | | | 5.49 |
| | $C_{23}H_{27}NO_4$ | 72.42 | 7.14 | | 72.58 | 7.18 | |
| 23 | $C_{20}H_{25}N$ | 85.97 | 9.02 | 5.01 | 86.12 | 9.13 | 5.27 |

Table II-continued
Analytical Data on Examples 9 to 25

| Example | Empirical Formula | Calculated C | H | N | Found C | H | N |
|---|---|---|---|---|---|---|---|
| 24 | $C_{27}H_{33}NO_4$ | 74.45 | 7.64 | | 74.47 | 7.67 | |
| 25 | $C_{24}H_{25}N$ | 88.02 | 7.70 | 4.28 | 88.28 | 7.48 | 4.46 |

[1]Nitrogen analysis of base; carbon and hydrogen analysis of maleate salt;
[2]Nitrogen analysis of free base; carbon and hydrogen analysis of maleate salt.

The invention further provides pharmaceutical compositions, comprising as active ingredient, at least one of the compounds according to the invention in association with a pharmaceutical carrier or excipient. The compounds may be presented in a form suitable for oral, parenteral or intracardial administration, or in a form suitable for inhalation. Thus, for example, compositions for oral administration are solid or liquid and can take the form of capsules, tablets, coated tablets, suspensions etc., employing such carriers or excipients conveniently used in the pharmaceutical art. Suitable tableting excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water, or a parenterally acceptable oil, e.g., arachis oil, contained in ampoules.

Advantageously, the compositions are formulated as dosage units, each unit being adapted to supply a fixed antiarrhythmic effective dose of active ingredient. Although very small quantities of the active materials of the present invention are effective when minor therapy is involved or in cases of administration to subjects having a relatively low body weight, unit dosages are usually from 5 milligrams or above and preferably 25, 50 or 100 milligrams or even higher, depending of course upon the emergency of the situation and the particular result desired. Five to 50 milligrams appears optimum per unit dose, or usual broader ranges appear to be 1 to 100 milligrams per unit dose. Daily dosages should preferably range from 10 mg. to 100 mg. It is only necessary that the active ingredient constitute an effective amount, i.e., such that a suitable effective dosage will be obtained, consistent with the dosage form employed. Obviously, several unit dosage forms may be administered at about the same time.

CAPSULES

| Ingredients: | | Per cap. mg. |
|---|---|---|
| 1. | Active ingredient | 5.0 |
| 2. | Lactose | 140.0 |
| 3. | Magnesium stearate | 4.0 |

Procedure:
1. Blend 1, 2 and 3.
2. Mill this blend and blend again.
3. This milled blend is then filled into No. 1 hard gelatin capsules.

TABLETS

| Ingredients: | | Mg./tabl. mg. |
|---|---|---|
| 1. | Active ingredient | 5.0 |
| 2. | Corn starch | 20.0 |
| 3. | Kelacid | 20.0 |
| 4. | Keltose | 20.0 |

TABLETS -continued

| Ingredients: | | Mg./tabl. mg. |
|---|---|---|
| 5. | Magnesium stearate | 1.5 |

Procedure:
1. Blend 1, 2, 3 and 4.
2. Add sufficient water portionwise to the blend from step No. 1 with careful stirring after each addition. Such additions of water and stirring continue until the mass is of a consistency to permit its conversion to wet granules.
3. The wet mass is converted to granules by passing it through the oscillating granulator, using 8-mesh screen.
4. The wet granules are then dried in an oven at 140° F.
5. The dried granules are then passed through an oscillating granulator, using a 10-mesh screen.
6. Lubricate the dry granules with 0.5% magnesium stearate.
7. The lubricated granules are compressed on a suitable tablet press.

INTRAVENOUS INJECTION

| Ingredients: | | | |
|---|---|---|---|
| 1. | Active ingredient | mg. | 5.0 |
| 2. | pH 4.0 buffer solution, q.s. to | ml. | 1.0 |

Procedure:
1. Dissolve the active ingredient in the buffer solution.
2. Aseptically filter the solution from Step No. 1.
3. The sterile solution is now aseptically filled into sterile ampoules.
4. The ampoules are sealed under aseptic conditions.

INTRAMUSCULAR INJECTION

| Ingredients: | | | |
|---|---|---|---|
| 1. | Active ingredient | mg. | 5.0 |
| 2. | Isotonic buffer solution 4.0, q.s. to | ml. | 2.0 |

Procedure:
1. Dissolve the active ingredient in the buffer solution.
2. Aseptically filter the solution from Step No. 1.
3. The sterile solution is now aseptically filled into sterile ampoules.
4. The ampoules are sealed under aseptic conditions.

INHALATION

| Ingredients: | | | |
|---|---|---|---|
| 1. | Active ingredient | mg. | 100 |
| 2. | Alcohol 95%, q.s. | cc. | 1.0 |

Procedure:
1. Dissolve No. 1 and No. 2.
2. This solution is properly packaged in an aerosol dispenser containing a metered valve and suitable propellant.

What is claimed is:

1. A method of controlling cardiac arrhythmias in a mammal suffering therewith which comprises administering to said mammal an antiarrhythmic effective amount of a compound of the formula:

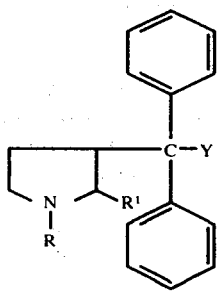

wherein;

R is a member selected from the group consisting of hydrogen, lower alkyl, lower cycloalkyl and phenyllower alkyl, R' is a member selected from the group consisting of hydrogen and lower alkyl, Y is a member selected from the group consisting of carbamoyl, cyano and hydrogen, and pharmaceutically acceptable acid addition salts thereof.

2. The method of claim 1 wherein R is lower alkyl.

3. The method of claim 2 wherein the compound is α,α-diphenyl-α-(1-isopropyl-3-pyrrolidinyl)acetamide.

4. The method of claim 2 wherein the compound is 3-benzhydryl-1-isobutylpyrrolidine.

5. The method of claim 1 wherein the compound is -(1-cyclohexyl-3-pyrrolidinyl)-α,α-diphenylacetamide.

* * * * *